(12) United States Patent
Karasawa

(10) Patent No.: US 8,529,508 B2
(45) Date of Patent: Sep. 10, 2013

(54) FLUID EJECTION DEVICE AND MEDICAL DEVICE

(75) Inventor: Junichi Karasawa, Shimosuwa-machi (JP)

(73) Assignee: Seiko Epson Corporation, Tokyo (JP)

(*) Notice: Subject to any disclaimer, the term of this patent is extended or adjusted under 35 U.S.C. 154(b) by 0 days.

(21) Appl. No.: 13/268,034

(22) Filed: Oct. 7, 2011

(65) Prior Publication Data
US 2012/0089090 A1    Apr. 12, 2012

(30) Foreign Application Priority Data

Oct. 8, 2010 (JP) .................................. 2010-228178
Jul. 5, 2011 (JP) .................................. 2011-148896

(51) Int. Cl.
    *A61M 37/00* (2006.01)
(52) U.S. Cl.
    USPC .......................................... 604/131; 222/251
(58) Field of Classification Search
    USPC .................. 604/131, 133; 222/251, 275, 282
    See application file for complete search history.

(56) References Cited

U.S. PATENT DOCUMENTS

| 7,901,374 B2 | 3/2011 | Seto et al. |
| 2003/0223886 A1* | 12/2003 | Keilman ........................ 417/229 |

FOREIGN PATENT DOCUMENTS

| JP | 02-095857 | 4/1990 |
| JP | 2008-082202 | 4/2008 |
| JP | 2012-107512 | 6/2012 |
| JP | 2012-107513 | 6/2012 |
| JP | 2012-115541 | 6/2012 |
| JP | 2012-167586 | 9/2012 |

* cited by examiner

*Primary Examiner* — Theodore Stigell
(74) *Attorney, Agent, or Firm* — Workman Nydegger

(57) ABSTRACT

A fluid ejection device includes: a pressure chamber; an actuator having a displacement plane that varies the volume of the pressure chamber; a delivery channel pipe communicating with the pressure chamber; a first reflection surface of pressure wave formed as part of a paraboloid of revolution that reflects a plane pressure wave by displacement of the actuator, the plane pressure wave propagating through the pressure chamber; and a second reflection surface of pressure wave formed as part of a paraboloid of revolution or an ellipsoid of revolution which is disposed so as to face the first reflection surface of pressure wave, wherein the first reflection surface of pressure wave and the second reflection surface of pressure wave have a common first focus, and a pressure wave reflected from the second reflection surface of pressure wave propagates through the delivery channel pipe and ejects fluid.

16 Claims, 7 Drawing Sheets

FLUID EJECTION DEVICE AND MEDICAL DEVICE

BACKGROUND

1. Technical Field

The present invention relates to fluid ejection devices and medical devices using the fluid ejection device.

2. Related Art

In the past, a fluid ejection device that converts fluid into a high-pressure pulsating current by varying the volume of a pressure chamber with a volume varying unit formed of a diaphragm and a piezoelectric element and pulsatively ejects the fluid at high velocity out of a nozzle by propagating a pressure wave through a delivery channel pipe from the pressure chamber has been proposed (see, for example, JP-A-2008-82202 (Patent Document 1)).

Moreover, a nozzleless inkjet fluid ejection device that ejects ink by forming, in the bottom of an ink chamber filled with ink, a paraboloidal reflecting plate from which acoustic energy is reflected, exciting a piezoelectric element provided on the ink surface, reflecting acoustic energy by the reflecting plate, and exciting the ink surface by concentrating the acoustic energy onto the focus of the paraboloid has been proposed (see, for example, JP-A-2-95857 (Patent Document 2)).

In the fluid ejection device structured as in Patent Document 1, a plane pressure wave generated in the pressure chamber by the driving of the piezoelectric element propagates through the pressure chamber and the delivery channel pipe communicating with the pressure chamber, the delivery channel pipe having a channel whose diameter is smaller than that of the pressure chamber. At this time, most of the plane pressure wave is reflected off an inner wall that surrounds the delivery channel pipe, the inner wall facing the piezoelectric element. Therefore, it is impossible to transfer the energy of the plane pressure wave to the inside of the delivery channel pipe efficiently.

On the other hand, it was believed that, in the structure as described in Patent Document 2, since the acoustic energy (incidentally, the acoustic energy can be replaced with the energy of the pressure wave) generated by the piezoelectric actuator was reflected from the reflecting plate and was converged onto the focus of the paraboloid located near the surface of the ink, the energy of the pressure wave could be concentrated onto the ink surface efficiently. However, since the acoustic energy which has been made to converge on the focus passes through the focus and then spreads radially because the focus of the paraboloid is provided in an ink ejection port, the ejected ink droplet sometimes breaks up, making it impossible to use the acoustic energy efficiently for ejecting the ink.

SUMMARY

An advantage of some aspects of the invention is to solve at least part of the problems described above, and the invention can be realized as forms or application examples described below.

Application Example 1

A fluid ejection device according to this application example includes: a pressure chamber; an actuator having a displacement plane that varies the volume of the pressure chamber; a delivery channel pipe communicating with the pressure chamber; a first reflection surface of pressure wave formed as part of a paraboloid of revolution that reflects a plane pressure wave by displacement of the actuator, the plane pressure wave propagating through the pressure chamber; and a second reflection surface of pressure wave formed as part of a paraboloid of revolution or an ellipsoid of revolution which is disposed so as to face the first reflection surface of pressure wave, wherein the first reflection surface of pressure wave and the second reflection surface of pressure wave have a common first focus, and a pressure wave reflected from the second reflection surface of pressure wave propagates through the delivery channel pipe and ejects fluid.

Here, the paraboloid of revolution is a plane formed by revolving a parabola 360 degrees about the symmetry axis thereof, and a central axis of rotation corresponds to the symmetry axis described above.

Here, the ellipsoid of revolution is a plane formed by revolving an ellipse 360 degrees about the major axis thereof, and a central axis of rotation corresponds to the major axis described above.

According to this application example, by driving the actuator, the plane pressure wave generated by the displacement plane of the actuator is made to converge on the first focus by the first reflection surface of pressure wave. The pressure wave which has converged propagates while spreading radially in the pressure chamber, is then reflected from the second reflection surface of pressure wave, and propagates through the delivery channel pipe. This makes it possible to transfer the pressure wave efficiently to the inside of the delivery channel pipe and use the energy of the pressure wave generated by the actuator for fluid ejection with high efficiency.

Incidentally, a common first focus in "the first reflection surface of pressure wave and the second reflection surface of pressure wave have a common first focus" in this application example means that there is no difference between the focus positions or there is a difference between the focus positions within the allowable range. The allowable range is within 10% of the distance between a point of intersection of the paraboloid of revolution or the ellipsoid of revolution including the second reflection surface of pressure wave and the central axis of rotation thereof and the first focus of the second reflection surface of pressure wave, in which it is expected that the effects of the invention will be obtained. Preferably, the allowable range is within 5% of the above distance, and, ideally, 0%, that is, there is no difference between the focus positions.

Application Example 2

In the fluid ejection device according to the application example described above, it is preferable that a central axis of rotation of the first reflection surface of pressure wave and a central axis of rotation of the second reflection surface of pressure wave be nearly parallel to each other.

In such a configuration, the central axes of rotation are disposed so as to be nearly parallel to each other. Therefore, the component elements have good symmetries, making it possible to make the plane pressure wave generated by the actuator propagate through the delivery channel pipe efficiently by the first reflection surface of pressure wave and the second reflection surface of pressure wave.

Incidentally, with such a configuration, it is possible to dispose the actuator, the pressure chamber, the first reflection surface of pressure wave, the second reflection surface of pressure wave, and the delivery channel pipe in a linear arrangement. This simplifies the structure and makes production easier.

Incidentally, the central axes of rotation which are nearly parallel mean that the central axes of rotation are parallel to each other or intersect within the allowable crossing angle range. The allowable crossing angle range is within ±5° in which it is expected that the effects of the invention will be obtained. Preferably, the allowable crossing angle range is within ±2.5°, and, ideally, 0°, that is, the central axes of rotation are parallel to each other (the same holds true for the following description).

Application Example 3

In the fluid ejection device according to the application example described above, it is preferable that the central axis of rotation of the first reflection surface of pressure wave and the central axis of rotation of the second reflection surface of pressure wave coincide with each other.

In such a configuration, the central axes of rotation are made to coincide with each other. Therefore, the component elements have good symmetries, making it possible to make the plane pressure wave generated by the actuator propagate through the delivery channel pipe more efficiently by the first reflection surface of pressure wave and the second reflection surface of pressure wave.

Incidentally, the central axes of rotation coinciding with each other mean that the central axes of rotation are nearly parallel to each other and there is no difference in positions of the central axes of rotation in a direction perpendicular to the central axes of rotation or there is a difference in positions of the central axes of rotation in a direction perpendicular to the central axes of rotation within the allowable range. The allowable range is within 10% of the distance between a point of intersection of the paraboloid of revolution or the ellipsoid of revolution including the second reflection surface of pressure wave and the central axis of rotation thereof and the first focus of the second reflection surface of pressure wave, in which it is expected that the effects of the invention will be obtained. Preferably, the allowable range is within 5% of the above distance, and, ideally, 0%, that is, there is no difference in positions of the central axes of rotation in a direction perpendicular to the central axes of rotation (the same holds true for the following description).

Application Example 4

In the fluid ejection device according to the application example described above, it is preferable that a central axis of rotation of the first reflection surface of pressure wave and a central axis of rotation of the second reflection surface of pressure wave be not parallel to each other.

With such a configuration, it is possible to make the pressure wave reflected from the second reflection surface of pressure wave propagate in a direction inclined to a direction in which the plane pressure wave generated by the actuator propagates. Thus, by making the central axis of the delivery channel pipe nearly parallel to the direction in which the pressure wave propagates, it is possible to realize a configuration of the fluid ejection device having the delivery channel pipe in a direction off the central axis of the displacement plane of the actuator and make the plane pressure wave generated by the actuator propagate through the pressure chamber and the delivery channel pipe efficiently.

Application Example 5

In the fluid ejection device according to the application example described above, it is preferable that a central axis of the displacement plane of the actuator and a central axis of rotation of the first reflection surface of pressure wave be nearly parallel to each other, and a central axis of the delivery channel pipe and a central axis of rotation of the second reflection surface of pressure wave be nearly parallel to each other.

In such a configuration, the central axis of rotation and the central axis of the displacement plane are made to be nearly parallel to each other, and the central axis of rotation and the central axis of the delivery channel pipe are made to be nearly parallel to each other. Therefore, the component elements have good symmetries, making it possible to make the plane pressure wave generated by the actuator propagate through the delivery channel pipe efficiently by the first reflection surface of pressure wave and the second reflection surface of pressure wave.

Incidentally, with such a configuration, it is possible to dispose the actuator, the first reflection surface of pressure wave, the second reflection surface of pressure wave, and the delivery channel pipe in a linear arrangement. This simplifies the structure and makes production easier.

Application Example 6

In the fluid ejection device according to the application example described above, it is preferable that the central axis of the displacement plane of the actuator and the central axis of rotation of the first reflection surface of pressure wave coincide with each other, and the central axis of the delivery channel pipe and the central axis of rotation of the second reflection surface of pressure wave coincide with each other.

In such a configuration, the central axis of rotation and the central axis of the displacement plane are made to coincide with each other, and the central axis of rotation and the central axis of the delivery channel pipe are made to coincide with each other. Therefore, the component elements have even better symmetries, making it possible to make the plane pressure wave generated by the actuator propagate through the delivery channel pipe more efficiently by the first reflection surface of pressure wave and the second reflection surface of pressure wave.

Application Example 7

In the fluid ejection device according to the application example described above, it is preferable that the central axis of the displacement plane of the actuator and the central axis of rotation of the first reflection surface of pressure wave be away from each other, and the central axis of the delivery channel pipe and the central axis of rotation of the second reflection surface of pressure wave be away from each other.

In such a configuration, the axes of the component elements are nearly parallel to each other and are away from each other. Therefore, the second reflection surface of pressure wave can reflect the pressure wave to a position which is nearly parallel to the plane pressure wave generated by the actuator, the position away from the plane pressure wave generated by the actuator, and make the pressure wave propagate through the delivery channel pipe which is also nearly parallel to the central axis of the displacement plane of the actuator and is away therefrom. This makes it possible to increase configuration flexibility of the fluid ejection device and transfer the pressure wave efficiently to the inside of the delivery channel pipe.

Application Example 8

In the fluid ejection device according to the application example described above, it is preferable that a second focus of the ellipsoid of revolution of the second reflection surface of pressure wave be disposed inside the delivery channel pipe.

In such a configuration, the pressure wave reflected from the second reflection surface of pressure wave converges on the second focus and spreads in the delivery channel pipe. Since the second focus is located inside the delivery channel pipe, the pressure wave spreading from the second focus propagates while being reflected from the inner wall of the delivery channel pipe. Also with such a configuration, it is possible to make the plane pressure wave generated by the actuator propagate through the pressure chamber and the delivery channel pipe efficiently.

Application Example 9

A medical device according to this application example employs the fluid ejection device described in any one of the application examples described above.

The medical device according to this application example can convert liquid into pulsed minuscule droplets and eject them at high velocity, and has excellent properties as a surgical instrument, such as causing no thermal damage when excising, incising, or crushing a living tissue and being capable of preserving a tubule tissue such as a blood vessel. Moreover, another advantage is that, when operations etc. are conducted by using the fluid ejection device described above, the amount of ejected liquid is small as compared to an existing device using a high-pressure flow, making it easy to see an operative site.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, embodiments of the invention will be described based on the drawings.

Incidentally, for the sake of illustration, the drawings which are referred to in the following description are schematic diagrams in which the shapes and the horizontal and vertical scale ratio of the component elements or portions are different from those of the actual component elements or portions, and the component elements or portions are shown in simplified forms to make the description understandable.

First Embodiment

Figure 1:
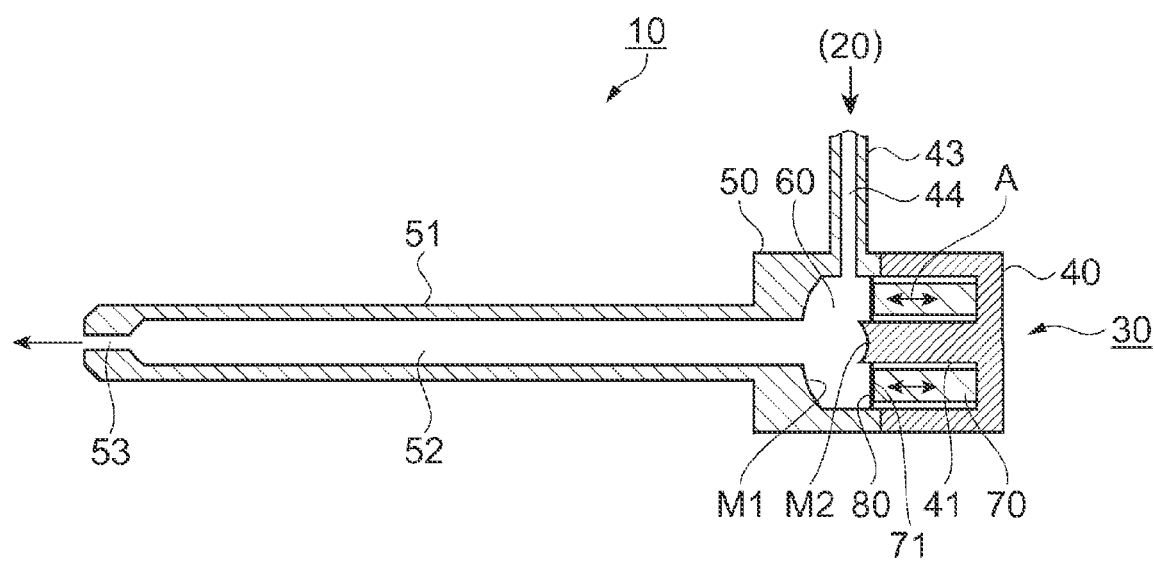
FIG. 1 is a sectional view showing the structure of a fluid ejection device according to a first embodiment.

FIG. 1 is a sectional view showing the structure of a fluid ejection device according to this embodiment. In FIG. 1, a fluid ejection device 10 includes a pressure generating section 30 having a pressure chamber 60 and an actuator 70 as a volume varying unit that varies the volume of the pressure chamber 60, a fluid supply pipe 43 having a fluid supply channel 44 communicating with the pressure chamber 60, and a delivery channel pipe 51 having a delivery channel 52 communicating with the pressure chamber 60.

The actuator 70 is a ring-shaped piezoelectric element. One end face of actuator 70 is fixed to an inner bottom face of a first machine casing 40, and the other end face is tightly fixed to a diaphragm 80 via a reinforcing member (not shown). By the application of a voltage, the other end face 71 (hereinafter referred to as a displacement plane 71) can stretch and shrink in the direction of an arrow A (the thickness direction). When the actuator 70 rapidly stretches and shrinks, a plane pressure wave is generated via the diaphragm 80. The outer edge of the diaphragm 80 is fixed to the first machine casing 40 or a second machine casing 50.

Incidentally, the actuator 70 is not limited to the piezoelectric element, and any element that can vary the volume of the pressure chamber 60 and generate a plane pressure wave can be used as the actuator 70.

In the center of the bottom face of the first machine casing 40, a projection penetrating the actuator 70 is formed, and, at the tip of the projection, a paraboloid of revolution is formed. The paraboloid of revolution will be referred to as a second reflection surface of pressure wave M2. Incidentally, the second reflection surface of pressure wave M2 juts from the displacement plane 71 of the actuator 70.

In FIG. 1, the fluid supply pipe 43 is formed in the second machine casing 50 so as to project therefrom; however, a structure in which the second machine casing 50 and the fluid supply pipe 43 are provided as separate components and the fluid supply pipe 43 is fixed to the second machine casing 50 by being press-fitted thereinto may be adopted. To the fluid supply pipe 43, a pump 20 as an unillustrated fluid supplying section is connected, and the pump 20 supplies fluid to the pressure chamber 60 at a constant pressure or a constant flow rate.

Incidentally, the first machine casing 40, the second machine casing 50, the fluid supply pipe 43, the delivery channel pipe 51, and a fluid ejection opening 53 are formed of sufficiently hard materials and possess stiffness which is high enough to prevent those components from being deformed by the pressure wave propagating through the fluid.

Moreover, in FIG. 1, in the second machine casing 50, the delivery channel pipe 51 is provided so as to project therefrom; however, a structure in which the second machine casing 50 and the delivery channel pipe 51 are provided as separate components and the delivery channel pipe 51 is fixed to the second machine casing 50 by being press-fitted thereinto may be adopted. At the tip of the delivery channel pipe 51, the fluid ejection opening 53 (which will be also referred to as a nozzle) whose channel diameter has a cross-sectional area which is smaller than the cross-sectional area of the delivery channel 52 is formed.

The first machine casing 40 and the second machine casing 50 are tightly fixed to each other at the faces at which the first machine casing 40 and the second machine casing 50 face each other, and a space surrounded by the inner wall of the second machine casing 50, the displacement plane 71 of the actuator 70, and the second reflection surface of pressure wave M2 is the pressure chamber 60. In addition, a face facing the displacement plane 71 and the second reflection surface of pressure wave M2 is a first reflection surface of pressure wave M1 formed as a paraboloid of revolution.

Next, fluid ejection action of the fluid ejection device 10 will be described with reference to FIG. 1. It is to be noted that description will be given on the assumption that the fluid is liquid. First, a drive waveform which is applied to drive the actuator 70 will be described.

Figure 2:
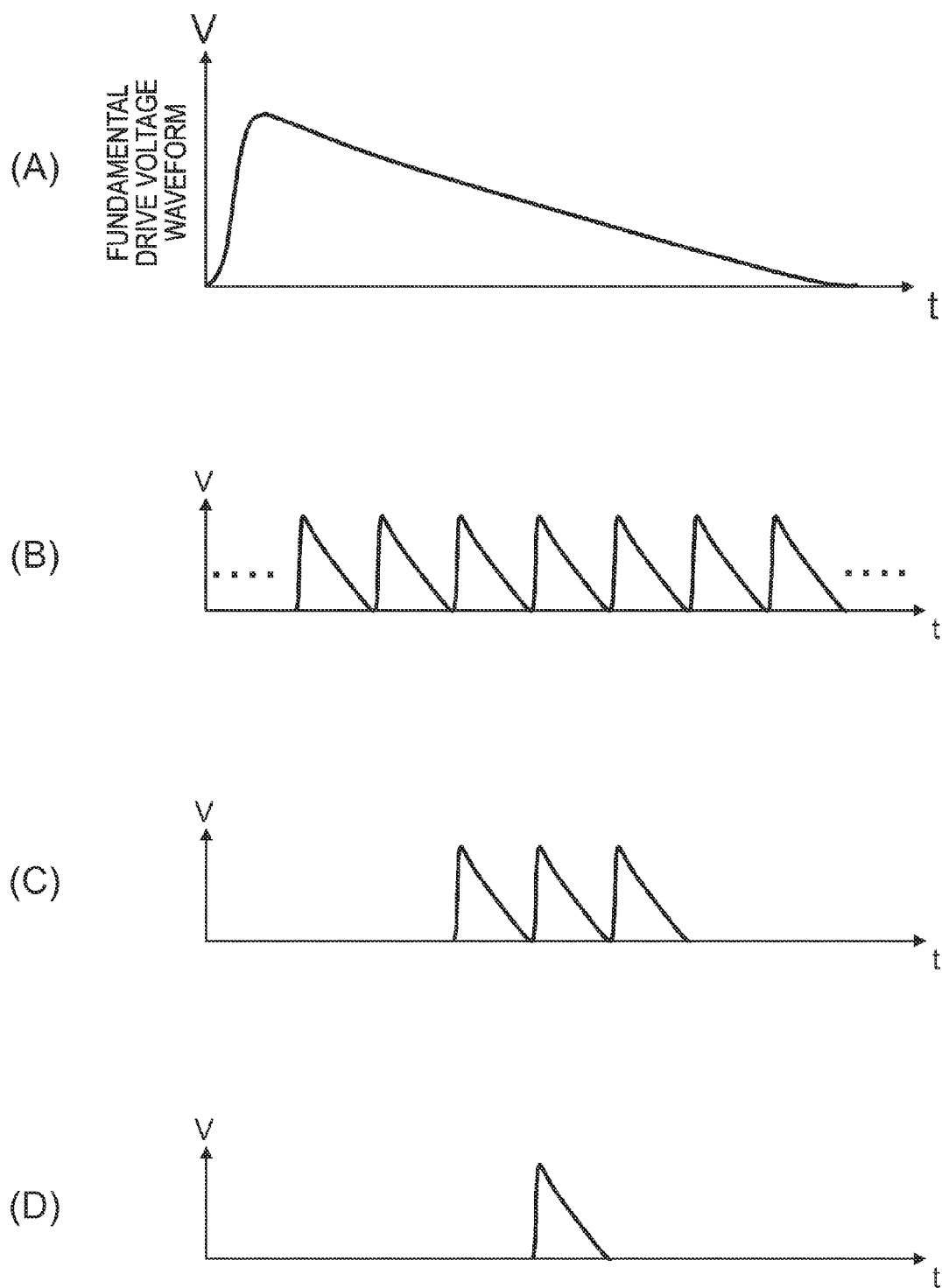
FIGS. 2A to 2D are voltage waveform diagrams driving an actuator according to the first embodiment.

FIG. 2A shows a fundamental drive voltage waveform diagram driving the actuator 70. As shown in FIG. 2A, the fundamental voltage waveform is a voltage waveform that rises sharply and falls gradually. In a rising region in which the drive voltage increases sharply, the actuator 70 rapidly stretches, and, in a falling region in which the drive voltage decreases gradually, the actuator 70 returns to its original length. This drive waveform is a fundamental voltage waveform driving the actuator 70.

When the fluid ejection device 10 is actually driven, the fundamental voltage waveform may be applied repeatedly with a certain period as shown in FIG. 2B or applied repeatedly for a finite number of times with a certain period as shown in FIG. 2C. Alternatively, as shown in FIG. 2D, the fundamental voltage waveform may be applied singly.

To the fluid supply channel 44, liquid is always supplied by the pump 20 at a constant pressure (or a constant flow rate). As a result, in a state in which the actuator 70 does not stretch and shrink, that is, in a steady state, the liquid with a constant flow rate that is determined by the supply pressure of the pump 20 and the channel resistance of the entire channel system extending from the fluid supply channel 44 to the fluid ejection opening 53 via the pressure chamber 60 and the delivery channel 52 flows from the pump 20 to the fluid ejection opening 53.

Here, suppose that a drive voltage is applied to the actuator 70 and the actuator 70 stretches rapidly. As a result, the volume of the pressure chamber 60 is rapidly reduced, and the pressure increases rapidly due to the compressibility of the fluid itself in the pressure chamber 60. The pressure which has been rapidly increased in the pressure chamber 60 starts propagating through the delivery channel 52 to the fluid ejection opening 53 as a pressure wave with an extremely large fluid displacement. The pressure wave propagates through the delivery channel 52 to the fluid ejection opening 53 at the velocity of sound propagating through the fluid, and is ejected as a high-speed jet when reaching the fluid ejection opening 53. Therefore, to eject a high-speed jet with high kinetic energy out of the fluid ejection opening 53, it is important to transfer the energy of the pressure wave provided by the rapid stretch of the actuator 70 to the fluid ejection opening 53 efficiently with the smallest possible loss.

Thus, the propagation of the pressure wave will be described with reference to FIG. 3.

Figure 3:
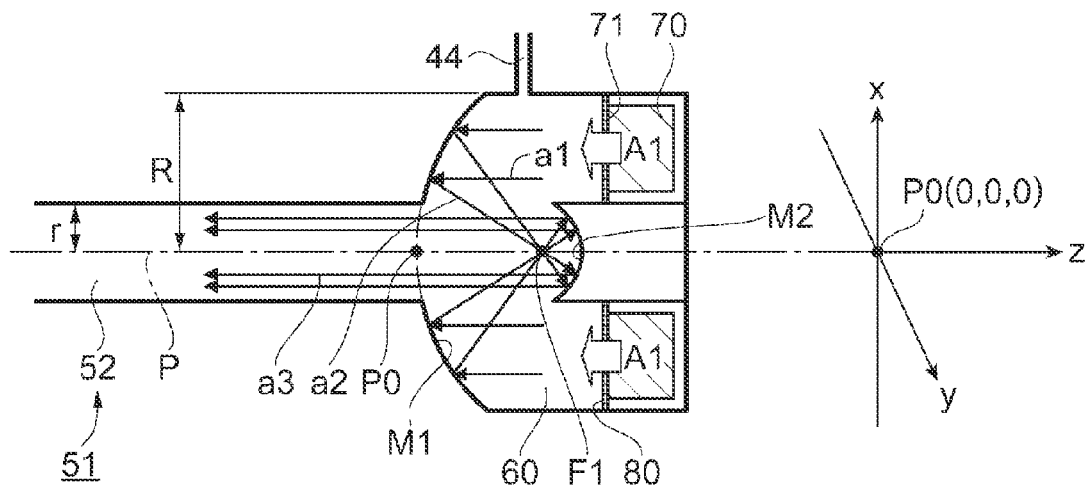
FIG. 3 is an explanatory diagram showing the propagation of a pressure wave according to the first embodiment.

FIG. 3 is an explanatory diagram showing the propagation of the pressure wave according to this embodiment. First, the relationship among the component elements will be described. In FIG. 3, the paraboloid of revolution of the first reflection surface of pressure wave M1 and the paraboloid of revolution of the second reflection surface of pressure wave M2 have a focus in common, and this focus is assumed to be a first focus F1. The central axes of rotation of the paraboloids of revolution of the first reflection surface of pressure wave M1 and the second reflection surface of pressure wave M2, the central axis of the displacement plane 71 of the actuator 70, and the central axis of the delivery channel pipe 51 coincide with each other (which are depicted as a P-axis in the drawing), and the first focus F1 is located on the P-axis. Incidentally, the P-axis is the same as a z-axis of a coordinate system.

Next, the shapes of the first reflection surface of pressure wave M1 and the second reflection surface of pressure wave M2 and the propagation of the pressure wave will be described with reference to FIG. 3 by using three-dimensional coordinate representation. The plane coordinates which are parallel to the displacement plane 71 are expressed by an x-axis and a y-axis, an axis perpendicular to the x-y plane is assumed to be a z-axis, and the coordinates are expressed as (x, y, z). The origin of coordinates P0(0, 0, 0) is assumed to be a point of intersection of the first reflection surface of pressure wave M1 and the P-axis, and, when the position of the first focus F1 is assumed to be (0, 0, f), the origin of coordinates P0(0, 0, 0) is assumed to be a vertex of the paraboloid of revolution which is the first reflection surface of pressure wave M1. Moreover, when the position of the first focus F1 is assumed to be (0, 0, f), the paraboloid of revolution of the first reflection surface of pressure wave M1 can be expressed by the following formulae.

$$Z = \frac{1}{4f}(x^2 + y^2) \quad (1)$$

$$r^2 \leq x^2 + y^2 \leq R^2 \quad (2)$$

Moreover, the paraboloid of revolution of the second reflection surface of pressure wave M2 can be expressed by the following formulae.

$$Z = -\frac{R}{4fr}(x^2 + y^2) + f\left(1 + \frac{r}{R}\right) \quad (3)$$

$$x^2 + y^2 \leq r^2 \quad (4)$$

Here, r is the radius of the delivery channel 52, and R is the peripheral radius of the actuator 70. However, it is assumed that R>r and f>R/2.

When the pressure chamber 60 is filled with the liquid, if the actuator 70 stretches rapidly (in the direction of an arrow A1), a plane pressure wave a1 is generated by the displacement plane 71. The generated plane pressure wave a1 propagates to the first reflection surface of pressure wave M1 (in the direction of an arrow a1) in the direction of the P-axis, and is reflected from the first reflection surface of pressure wave M1. The reflected pressure wave a2 propagates in the direction of an arrow a2, spreads to the second reflection surface of pressure wave M2 after converging on the first focus F1, and is then reflected from the second reflection surface of pressure wave M2. Since the first focus F1 is a common focus of the paraboloid of revolution of the first reflection surface of pressure wave M1 and the paraboloid of revolution of the second reflection surface of pressure wave M2, the pressure wave a3 reflected from the second reflection surface of pressure wave M2 propagates through the delivery channel 52 in the direction of the P-axis (in the direction of an arrow a3).

Incidentally, the shapes and placement of the paraboloid of revolution of the first reflection surface of pressure wave M1 and the paraboloid of revolution of the second reflection surface of pressure wave M2 are set so that a line segment connecting an edge portion (the outermost edge) of the paraboloid of revolution of the first reflection surface of pressure wave M1 and the first focus F1 does not intersect with the second reflection surface of pressure wave M2. That is, the pressure wave transfer path is set so that the pressure wave reflected from the first reflection surface of pressure wave M1 is not blocked by the second reflection surface of pressure wave M2 itself.

Therefore, according to this embodiment, the plane pressure wave a1 generated by the displacement plane 71 by driving the actuator 70 is made to converge on the first focus F1 by the first reflection surface of pressure wave M1. The pressure wave which has converged propagates in the pressure chamber 60 while spreading radially, enters the second reflection surface of pressure wave M2, is reflected from the paraboloid of revolution of the second reflection surface of pressure wave M2, and propagates through the delivery channel pipe 51 (the delivery channel 52). By doing so, it is possible to transfer the pressure wave efficiently to the inside of the delivery channel pipe 51 and use the energy of the pressure wave generated by the actuator 70 for fluid ejection with high efficiency.

Moreover, in this embodiment, the central axes of rotation of the first reflection surface of pressure wave M1 and the second reflection surface of pressure wave M2, the central axis of the displacement plane 71, and the central axis of the delivery channel pipe 51 are made to coincide with each other. As a result, the component elements have good symmetries, making it possible to make the plane pressure wave generated by the actuator 70 propagate through the delivery channel pipe 51 efficiently by the first reflection surface of pressure wave M1 and the second reflection surface of pressure wave M2.

Incidentally, with this structure, it is possible to place the actuator 70, the pressure chamber 60, the first reflection surface of pressure wave M1, the second reflection surface of pressure wave M2, and the delivery channel pipe 51 in a linear arrangement. This simplifies the structure and makes production easier.

Incidentally, the common first focus F1 of the first reflection surface of pressure wave M1 and the second reflection surface of pressure wave M2 in this embodiment means that there is no difference between the focus positions of the first reflection surface of pressure wave M1 and the second reflection surface of pressure wave M2 or there is a difference between the focus positions within the allowable range. The allowable range is within 10% of the distance between a point of intersection of the second reflection surface of pressure wave M2 and the P-axis and the first focus F1, in which it is expected that the effects of this embodiment will be obtained. Preferably, the allowable range is within 5% of the above distance, and, ideally, 0%, that is, there is no difference between the focus positions of the first reflection surface of pressure wave M1 and the second reflection surface of pressure wave M2.

The evaluation by an experiment has confirmed that the pressure wave is efficiently transferred to the inside of the delivery channel pipe 51 when the allowable range is within 10% of the distance between the point of intersection of the second reflection surface of pressure wave M2 and the P-axis and the first focus F1 since an angle at which the pressure wave reflected from the second reflection surface of pressure wave M2 strikes the wall surface of the delivery channel pipe 51 when passing through the delivery channel pipe 51 is kept within an angle of incidence of 6 degrees as compared to a case in which the allowable range exceeds 10% and an angle at which the pressure wave reflected from the second reflection surface of pressure wave M2 strikes the wall surface of the delivery channel pipe 51 when passing through the delivery channel pipe 51 exceeds an angle of incidence of 6 degrees. Moreover, it has been confirmed that the efficiency is expressly improved when the allowable range is within 2% of the distance between the point of intersection of the second reflection surface of pressure wave M2 and the P-axis and the first focus F1 (the same holds true for the following description).

Moreover, the central axes of rotation which are nearly parallel to each other mean that the central axes of rotation are parallel to each other or intersect within the allowable crossing angle range. The allowable crossing angle range is within ±5° in which it is expected that the effects of this embodiment will be obtained. Preferably, the allowable crossing angle range is within ±2.5°, and, ideally, 0°, that is, the central axes of rotation are parallel to each other (the same holds true for the following description).

Furthermore, the central axes of rotation coinciding with each other mean that the central axes of rotation are nearly parallel to each other and there is no difference in positions of the central axes of rotation in a direction perpendicular to the central axes of rotation or there is a difference in positions of the central axes of rotation in a direction perpendicular to the central axes of rotation within the allowable range. The allowable range is within 10% of the distance between the point of intersection of the second reflection surface of pressure wave M2 and the P-axis and the first focus F1, in which it is expected that the effects of this embodiment will be obtained. Preferably, the allowable range is within 5% of the above distance, and, ideally, 0%, that is, there is no difference in positions of the central axes of rotation in a direction perpendicular to the central axes of rotation (the same holds true for the following description). This is the same as the evaluation by the experiment conducted on the first focus F1.

Second Embodiment

Next, a fluid ejection device according to a second embodiment will be described with reference to the drawing. Unlike the first embodiment described above (see FIG. 3), the features of the second embodiment are that the second reflection surface of pressure wave M2 is formed as an ellipsoid of revolution, and a second focus located on the major axis of the ellipsoid of revolution exists inside the delivery channel pipe 51. Therefore, only differences from the first embodiment are explained, and such elements as are found also in the first embodiment will be identified with the same reference characters.

Figure 4:
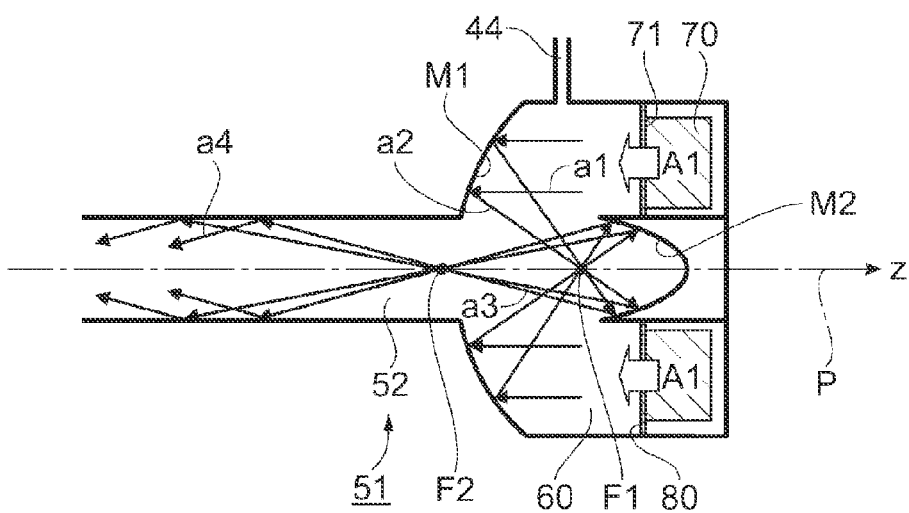
FIG. 4 is an explanatory diagram showing the propagation of a pressure wave according to a second embodiment.

FIG. 4 is an explanatory diagram showing the propagation of a pressure wave according to this embodiment. In FIG. 4, the first reflection surface of pressure wave M1 is formed as a paraboloid of revolution, and the second reflection surface of pressure wave M2 is formed as an ellipsoid of revolution. In this embodiment, the central axis of the displacement plane 71 of the actuator 70, the central axes of rotation of the first reflection surface of pressure wave M1 and the second reflection surface of pressure wave M2, and the central axis of the delivery channel pipe 51 are located on a common axis (a P-axis).

The focus of the paraboloid of revolution of the first reflection surface of pressure wave M1 is the same as one of the focuses of the ellipsoid of revolution of the second reflection surface of pressure wave M2, and this common focus is referred to as a first focus F1. In addition, the ellipsoid of revolution of the second reflection surface of pressure wave M2 has a second focus F2 on the major axis thereof in a position farther away from the ellipsoid of revolution of the second reflection surface of pressure wave M2 than the first focus F1, and the second focus F2 is disposed inside the delivery channel 52.

In such a configuration, when the actuator 70 stretches rapidly (in the direction of an arrow A1), a plane pressure wave a1 is generated by the displacement plane 71, and the generated plane pressure wave a1 propagates to the first reflection surface of pressure wave M1 in parallel to the P-axis and is reflected from the first reflection surface of pressure wave M1. After converging on the first focus F1, the reflected pressure wave a2 spreads to the second reflection surface of pressure wave M2, enters the second reflection surface of pressure wave M2, and is then reflected therefrom. After converging on the second focus F2, the pressure wave a3 reflected from the second reflection surface of pressure wave M2 spreads, reaches the inner wall of the delivery channel pipe 51, and propagates through the delivery channel 52 while being reflected from the inner wall (this reflected pressure wave is shown as a pressure wave a4).

Since the second focus F2 is disposed in the delivery channel pipe 51 (the delivery channel 52), the pressure wave a3 propagates through the delivery channel pipe 51. Therefore, the pressure wave a3 reflected from the second reflection surface of pressure wave M2 converges in the delivery channel pipe 51.

Incidentally, the shapes and placement of the paraboloid of revolution of the first reflection surface of pressure wave M1 and the ellipsoid of revolution of the second reflection surface of pressure wave M2 are set so that a line segment connecting an edge portion (the outermost edge) of the paraboloid of revolution of the first reflection surface of pressure wave M1 and the first focus F1 does not intersect with the second reflection surface of pressure wave M2. That is, the pressure wave transfer path is set so that the pressure wave reflected from the first reflection surface of pressure wave M1 is not blocked by the second reflection surface of pressure wave M2 itself.

Moreover, the shapes and placement of the paraboloid of revolution of the first reflection surface of pressure wave M1 and the ellipsoid of revolution of the second reflection surface of pressure wave M2 are set so that a line segment connecting an edge portion (the outermost edge) of the ellipsoid of revolution of the second reflection surface of pressure wave M2 and the second focus F2 does not intersect with the inner wall surface of the delivery channel pipe 51. That is, the pressure wave transfer path is set so that most of the pressure wave reflected from the second reflection surface of pressure wave M2 enters the delivery channel pipe 51.

Therefore, according to this embodiment, the pressure wave reflected from the second reflection surface of pressure wave M2 converges on the second focus F2 and then spreads in the delivery channel pipe 51. Since the second focus F2 is located in the delivery channel pipe 51, the pressure wave spreading from the second focus F2 propagates while being reflected from the inner wall of the delivery channel pipe 51. Also with such a configuration, it is possible to make the plane pressure wave generated by the actuator 70 propagate through the delivery channel pipe 51 efficiently by the first reflection surface of pressure wave M1 and the second reflection surface of pressure wave M2.

Third Embodiment

Next, a fluid ejection device according to a third embodiment will be described with reference to the drawings. Unlike the first embodiment described above (see FIG. 3), the features of the third embodiment are that the central axes of rotation of the paraboloid of revolution of the first reflection surface of pressure wave M1 and the paraboloid of revolution of the second reflection surface of pressure wave M2 coincide with each other, the central axis of the delivery channel pipe 51, the central axis of the displacement plane 71 of the actuator 70, and the central axes of rotation of the paraboloid of revolution of the first reflection surface of pressure wave M1 and the paraboloid of revolution of the second reflection surface of pressure wave M2 are nearly parallel to one another and are away from one another. Therefore, only differences from the first embodiment are explained, and such elements as find their functionally equivalent counterparts in the first embodiment will be identified with the same reference characters.

Figure 5:
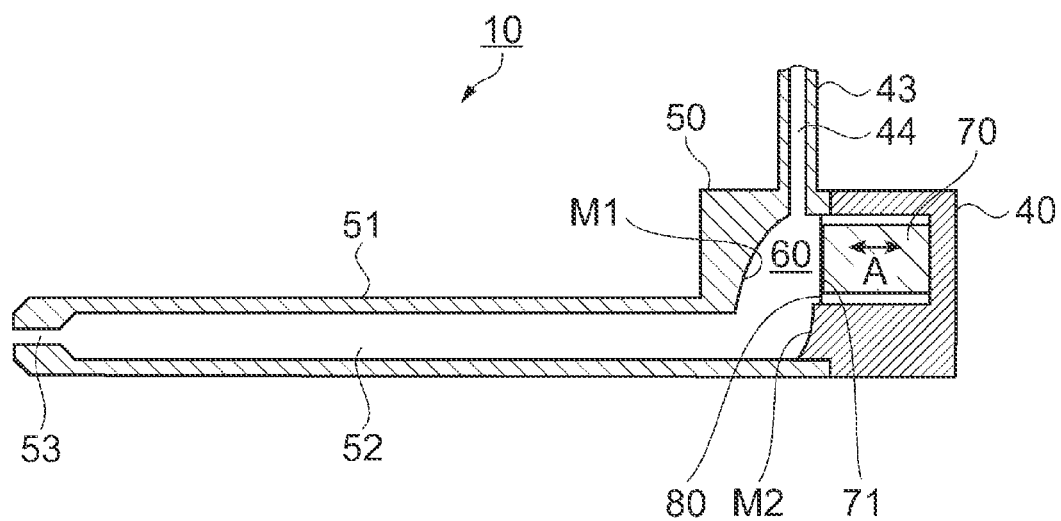
FIG. 5 is a sectional view showing the structure of a fluid ejection device according to a third embodiment.

FIG. 5 is a sectional view showing the structure of the fluid ejection device according to this embodiment. In FIG. 5, the central axis of rotation of the paraboloid of revolution of the first reflection surface of pressure wave M1 and the central axis of rotation of the paraboloid of revolution of the second reflection surface of pressure wave M2 coincide with each other. In addition, the central axis of the delivery channel pipe 51, the central axis of the displacement plane 71 of the actuator 70, and the central axes of rotation of the paraboloid of revolution of the first reflection surface of pressure wave M1 and the paraboloid of revolution of the second reflection surface of pressure wave M2 are nearly parallel to one another and are away from one another. Therefore, as shown in FIG. 5, the actuator 70 has a columnar shape having the displacement plane 71 and is located so as to be nearly parallel to the central axes of rotation of the first reflection surface of pressure wave M1 and the second reflection surface of pressure wave M2.

Next, the propagation of a pressure wave in the fluid ejection device 10 structured as described above will be described with reference to FIG. 6.

Figure 6:
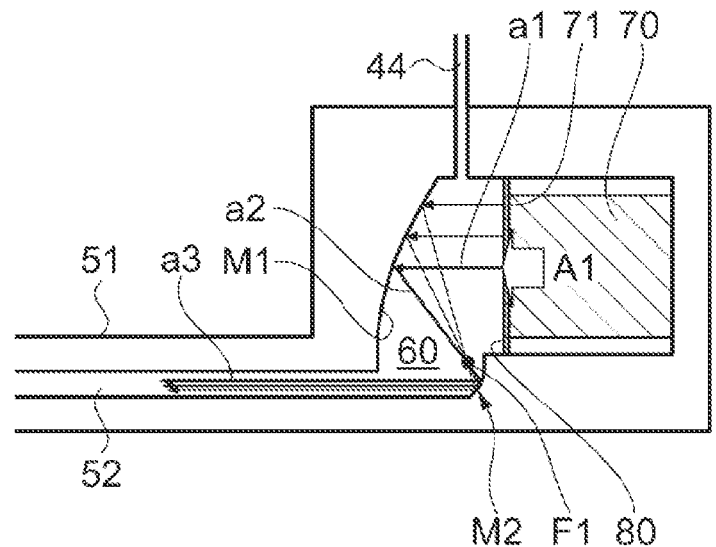
FIG. 6 is an explanatory diagram showing the propagation of a pressure wave according to the third embodiment.

FIG. 6 is an explanatory diagram showing the propagation of a pressure wave according to this embodiment. When the pressure chamber 60 is filled with liquid, if the actuator 70 stretches rapidly (in the direction of an arrow A1), a plane pressure wave is generated by the displacement plane 71, and the generated plane pressure wave propagates to the first reflection surface of pressure wave M1 in a direction nearly parallel to the central axis of the displacement plane 71 (in the direction of an arrow a1), and is reflected from the first reflection surface of pressure wave M1. After converging on the first focus F1, the reflected pressure wave spreads in the direction of the second reflection surface of pressure wave M2 (in the direction of an arrow of a2), and is reflected from the second reflection surface of pressure wave M2. Since the first focus F1 is a common focus of the paraboloid of revolution of the first reflection surface of pressure wave M1 and the paraboloid of revolution of the second reflection surface of pressure wave M2, the pressure wave reflected from the second reflection surface of pressure wave M2 propagates through the delivery channel 52 in the direction of the central axis of the delivery channel pipe 51 (in the direction of an arrow a3).

Therefore, according to this embodiment, the central axis of the delivery channel pipe 51, the central axis of the displacement plane 71 of the actuator 70, and the central axes of rotation of the paraboloid of revolution of the first reflection surface of pressure wave M1 and the paraboloid of revolution of the second reflection surface of pressure wave M2 are in a state in which they are offset. Thus, the pressure wave a2 reflected from the first reflection surface of pressure wave M1 propagates in a direction which is away from the displacement plane 71 in a planar direction, and enters the second reflection surface of pressure wave M2. The second reflection surface of pressure wave M2 can reflect the pressure wave in nearly parallel to the plane pressure wave a1 generated by the actuator 70 and make the pressure wave propagate through the delivery channel pipe 51 which is also located in a position nearly parallel to the central axis of the displacement plane 71 and away therefrom. This makes it possible to increase configuration flexibility of the fluid ejection device 10 and transfer the pressure wave efficiently to the inside of the delivery channel pipe 51.

Fourth Embodiment

Next, a fluid ejection device according to a fourth embodiment will be described with reference to the drawing. Unlike the third embodiment described above (see FIG. 5), the features of the fourth embodiment are that the second reflection surface of pressure wave M2 is formed as an ellipsoid of revolution, and a second focus F2 located on the major axis of the ellipsoid of revolution exists inside the delivery channel pipe 51. Therefore, only differences from the third embodiment are explained, and such elements as are found also in the third embodiment will be identified with the same reference characters.

Figure 7:
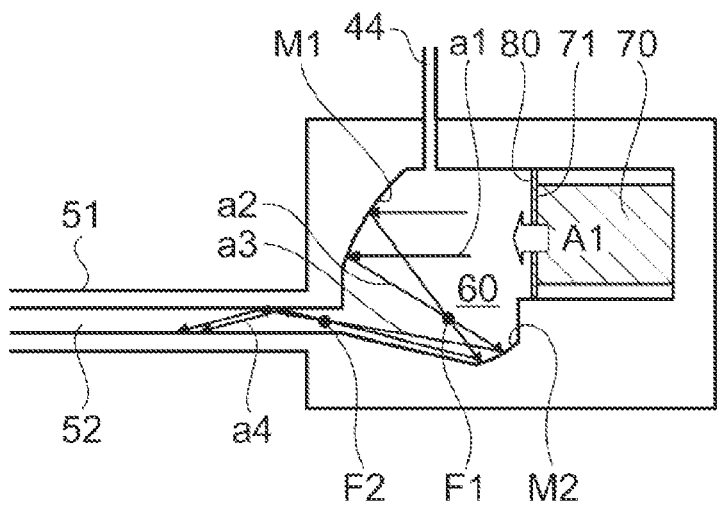
FIG. 7 is a sectional view showing the structure of a fluid ejection device according to a fourth embodiment and the propagation of a pressure wave.

FIG. 7 is a sectional view showing the structure of the fluid ejection device according to this embodiment and the propagation of a pressure wave. In FIG. 7, the first reflection surface of pressure wave M1 is formed as a paraboloid of revolution, and the second reflection surface of pressure wave M2 is formed as an ellipsoid of revolution. The central axis of rotation of the paraboloid of revolution of the first reflection surface of pressure wave M1 and the central axis of rotation of the ellipsoid of revolution of the second reflection surface of pressure wave M2 coincide with each other. In addition, the central axis of the delivery channel pipe 51, the central axis of the displacement plane 71 of the actuator 70, the central axis of the paraboloid of revolution of the first reflection surface of pressure wave M1, and the central axis of rotation of the ellipsoid of revolution of the second reflection surface of pressure wave M2 are nearly parallel to one another and are away from one another.

The focus of the paraboloid of revolution of the first reflection surface of pressure wave M1 is the same as one of the focuses of the ellipsoid of revolution of the second reflection surface of pressure wave M2, and this common focus is referred to as a first focus F1. In addition, the ellipsoid of revolution of the second reflection surface of pressure wave M2 has a second focus F2 on the major axis thereof in a position farther away from the ellipsoid of revolution of the second reflection surface of pressure wave M2 than the first focus F1, and the second focus F2 is disposed inside the delivery channel pipe 51.

With this structure, when the actuator 70 stretches rapidly (in the direction of an arrow A1), a plane pressure wave is generated by the displacement plane 71, and the generated plane pressure wave propagates in the direction of the first reflection surface of pressure wave M1 (in the direction of an arrow a1) and is reflected from the first reflection surface of pressure wave M1. After converging on the first focus F1, the reflected pressure wave spreads to the second reflection surface of pressure wave M2 (in the direction of an arrow a2), enters the second reflection surface of pressure wave M2, and is reflected therefrom. After converging on the second focus F2, the pressure wave reflected from the second reflection surface of pressure wave M2 spreads, reaches the inner wall of the delivery channel pipe 51, and propagates through the delivery channel 52 while being reflected from the inner wall (the pressure wave is shown by an arrow a4).

Since the second focus F2 is disposed in the delivery channel pipe 51 (in the delivery channel 52), a pressure wave a3 propagates through the delivery channel pipe 51. Therefore, the pressure wave a3 reflected from the second reflection surface of pressure wave M2 is made to converge in the delivery channel pipe 51.

According to this embodiment, the second reflection surface of pressure wave M2 formed as an ellipsoid of revolution has the second focus F2 in the delivery channel pipe 51. Therefore, the pressure wave which has converged on the second focus F2 propagates while being reflected from the inner wall of the delivery channel pipe 51. Also with such a configuration, it is possible to make the plane pressure wave generated by the actuator 70 propagate through the delivery channel pipe 51 efficiently.

Fifth Embodiment

Next, a fluid ejection device according to a fifth embodiment will be described with reference to the drawings. Unlike the first embodiment described above (see FIG. 1), in the fifth embodiment, the central axes of rotation of the paraboloid of revolution of the first reflection surface of pressure wave M1 and the paraboloid of revolution of the second reflection surface of pressure wave M2 are not parallel to each other (however, there is a common point/a point of intersection of these central axes, which is a focus only). In addition, the features of the fifth embodiment are that the central axis of the displacement plane 71 of the actuator 70 and the central axis of rotation of the first reflection surface of pressure wave M1 are nearly parallel to each other, and the central axis of rotation of the second reflection surface of pressure wave M2 and the central axis of the delivery channel pipe 51 are nearly parallel to each other. Therefore, only differences from the first embodiment are explained, and such elements as find their functionally equivalent counterparts in the first embodiment will be identified with the same reference characters.

Figure 8:
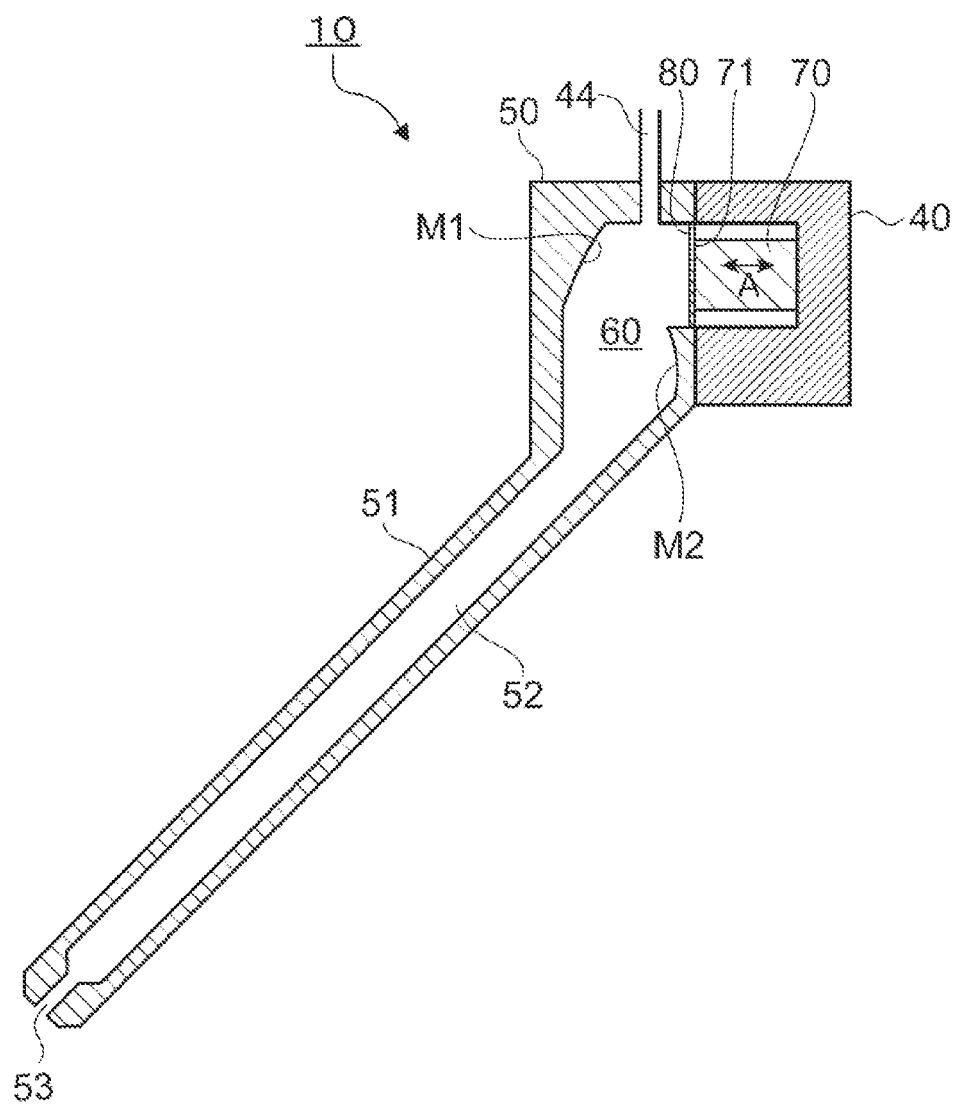
FIG. 8 is a sectional view showing the structure of a fluid ejection device according to a fifth embodiment.

FIG. 8 is a sectional view showing the structure of the fluid ejection device according to this embodiment. In FIG. 8, the central axis of rotation of the paraboloid of revolution of the first reflection surface of pressure wave M1 and the central axis of rotation of the paraboloid of revolution of the second reflection surface of pressure wave M2 are not parallel to each other. In addition, the central axis of the delivery channel pipe 51, the central axis which is nearly parallel to the central axis of rotation of the second reflection surface of pressure wave M2, and the central axis of the displacement plane 71 of the actuator 70, the central axis which is nearly parallel to the central axis of rotation of the first reflection surface of pressure wave M1, are displaced from each other. The actuator 70 has a columnar shape having the displacement plane 71, and is disposed so as to be nearly parallel to the central axis of rotation of the first reflection surface of pressure wave M1.

Moreover, since the central axis of the delivery channel pipe 51 and the central axis of rotation of the paraboloid of revolution of the first reflection surface of pressure wave M1 are displaced from each other, the delivery channel pipe 51 is provided so as to extend and be inclined with respect to a displacement direction of the actuator 70 (a direction of an arrow A).

Next, the propagation of a pressure wave in the fluid ejection device 10 structured as described will be described with reference to FIG. 9.

Figure 9:
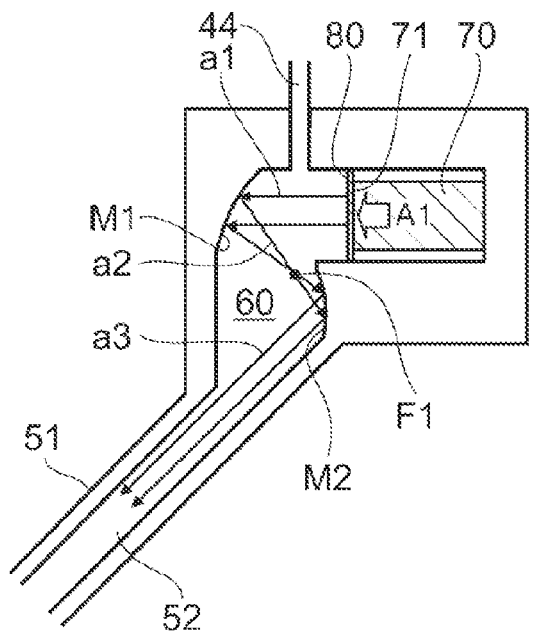
FIG. 9 is an explanatory diagram showing the propagation of a pressure wave according to the fifth embodiment.

FIG. 9 is an explanatory diagram showing the propagation of the pressure wave according to this embodiment. When the pressure chamber 60 is filled with liquid, if the actuator 70 stretches rapidly (in the direction of an arrow A1), a plane pressure wave is generated by the displacement plane 71, and the generated plane pressure wave propagates in a vertical direction with respect to the displacement plane 71 to the first reflection surface of pressure wave M1 (in the direction of an arrow a1), and is reflected from the first reflection surface of pressure wave M1. After converging on the first focus F1, the reflected pressure wave spreads to the second reflection surface of pressure wave M2 (in the direction of an arrow a2), and is reflected from the second reflection surface of pressure wave M2. Since the first focus F1 is a common focus of the paraboloid of revolution of the first reflection surface of pressure wave M1 and the paraboloid of revolution of the second reflection surface of pressure wave M2 and the second reflection surface of pressure wave M2 is formed as a paraboloid of revolution, the pressure wave travels in a direction (in the direction of an arrow a3) inclined to the direction (the direction of the arrow a1) in which the plane pressure wave propagates. Since the delivery channel pipe 51 is provided so as extend in the same direction as the direction in which the pressure wave travels, the pressure wave propagates through the delivery channel pipe 51.

The pressure wave a3 reflected from the second reflection surface of pressure wave M2 propagates in a direction inclined to the direction in which the plane pressure wave a1 generated by the actuator 70 propagates. Thus, by making the central axis of the delivery channel pipe 51 coincide with the direction in which the pressure wave a3 propagates, it is possible to realize a configuration of the fluid ejection device 10 having the delivery channel pipe 51 in a position off the central axis of the displacement plane 71 of the actuator 70 in an intended inclined direction and make the pressure wave generated by the actuator 70 propagate through the delivery channel pipe 51 efficiently.

Sixth Embodiment

Next, a fluid ejection device according to a sixth embodiment will be described with reference to the drawing. Unlike the fifth embodiment described above (see FIG. 8), the features of the sixth embodiment are that the second reflection surface of pressure wave M2 is formed as an ellipsoid of revolution, and a second focus F2 located on the major axis of the ellipsoid of revolution exists inside the delivery channel pipe 51 (the delivery channel 52). Therefore, only differences from the fifth embodiment are explained, and such elements as are found also in the fifth embodiment will be identified with the same reference characters.

Figure 10:
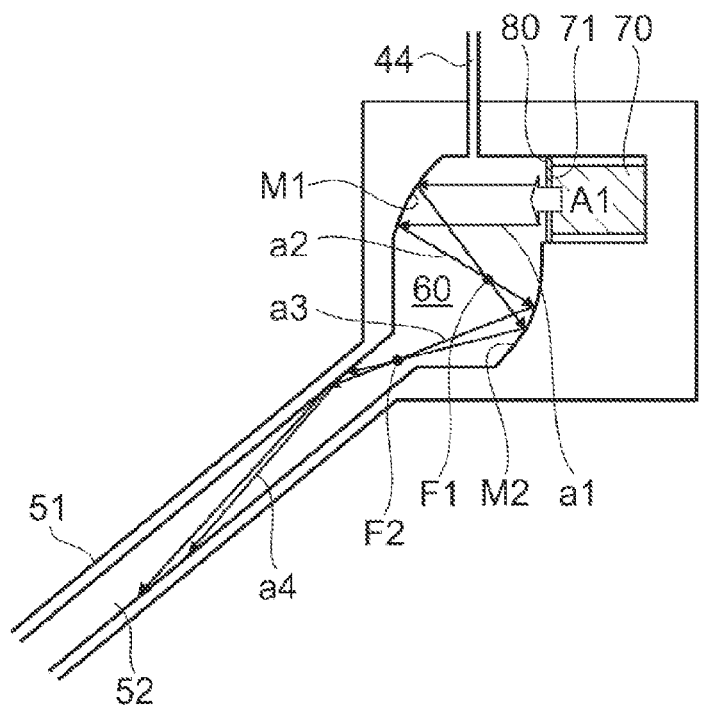
FIG. 10 is a sectional view showing the structure of a fluid ejection device according to a sixth embodiment and the propagation of a pressure wave.

FIG. 10 is a sectional view showing the structure of the fluid ejection device according to this embodiment and the propagation of a pressure wave. In FIG. 10, the first reflection surface of pressure wave M1 is formed as a paraboloid of revolution, and the second reflection surface of pressure wave M2 is formed as an ellipsoid of revolution. The central axis of rotation of the paraboloid of revolution of the first reflection surface of pressure wave M1 and the central axis of rotation of the ellipsoid of revolution of the second reflection surface of pressure wave M2 are not parallel to each other (however, there is a common point/a point of intersection of these central axes, which is a focus only). In addition, the central axis of the displacement plane 71 of the actuator 70 and the central axis of rotation of the first reflection surface of pressure wave M1 are nearly parallel to each other, and the central axis of rotation of the second reflection surface of pressure wave M2 and the central axis of the delivery channel pipe 51 are nearly parallel to each other.

The focus of the paraboloid of revolution of the first reflection surface of pressure wave M1 is the same as one of the focuses of the ellipsoid of revolution of the second reflection surface of pressure wave M2, and this common focus is referred to as a first focus F1. In addition, the ellipsoid of revolution of the second reflection surface of pressure wave M2 has a second focus F2 on the major axis thereof, and the second focus F2 is disposed inside the delivery channel pipe 51.

With this structure, when the actuator 70 stretches rapidly (in the direction of an arrow A1), a plane pressure wave a1 is generated by the displacement plane 71, and the generated plane pressure wave a1 propagates to the first reflection surface of pressure wave M1 and is reflected from the first reflection surface of pressure wave M1. After converging on the first focus F1, the reflected pressure wave a2 spreads to the second reflection surface of pressure wave M2, enters the second reflection surface of pressure wave M2, and is reflected therefrom. After converging on the second focus F2, the pressure wave a3 reflected from the second reflection surface of pressure wave M2 spreads, reaches the inner wall of the delivery channel pipe 51, and propagates through the delivery channel 52 while being reflected from the inner wall (this reflected pressure wave is shown as a pressure wave a4).

Since the second focus F2 is disposed in the delivery channel pipe 51 (the delivery channel 52), the pressure wave a3 propagates through the delivery channel pipe 51. Therefore, the pressure wave a3 reflected from the second reflection surface of pressure wave M2 is made to converge in the delivery channel pipe 51.

The second reflection surface of pressure wave M2 has the second focus F2 in the delivery channel pipe 51. Therefore, the pressure wave which has converged on the second focus F2 propagates while being reflected from the inner wall of the delivery channel pipe 51. This makes it possible to make the pressure wave generated by the actuator 70 propagate through the delivery channel pipe 51 efficiently.

Incidentally, the fluid ejection device 10 described above can be applied to a unit of transporting and ejecting a minute amount of liquid such as ink or a chemical solution and can be applied to cleaning etc. of a tubule or a minute gap of a medical device, a living body, and an apparatus. As a typical example, cooling devices and medical devices will be described.

Cooling Devices

Cooling devices use the fluid ejection devices described in the first to sixth embodiments described above. These fluid ejection devices 10 discharge a series of pulsed minuscule droplets at high velocity out of the fluid ejection opening (the nozzle) 53 by intermittently driving the actuator 70. Specifically, cooling by the ejection of pulsed minuscule droplets includes a cooling medium for cooling a heat source such as a solid light source and a cooling medium cooling unit cooling the cooling medium whose temperature has been increased as a result of absorbing the amount of heat generated by the heat source. In addition, such a cooling device has an advantage that the cooling medium cooling unit is driven for the duration corresponding to the amount of heat generation of a heating element from the viewpoint of reducing noise during cooling and achieving power savings.

Medical Devices

Medical devices use the fluid ejection devices described in the first to sixth embodiments described above. These fluid ejection devices 10 eject a series of pulsed minuscule droplets at high velocity out of the fluid ejection opening (the nozzle) 53 by intermittently driving the actuator 70. Operations conducted by using ejection of pulsed minuscule droplets have excellent properties as operative procedures, such as causing no thermal damage when excising, incising, or crushing a living tissue and being capable of selectively excising and preserving a living tissue. Moreover, another advantage is that, when operations etc. are conducted by using such a fluid ejection device 10, the amount of ejected liquid is small as compared to an existing device using a high-pressure steady flow, making it easy to see an operative site.

This application claims priority to Japanese Patent Application No. 2010-228178, filed on Oct. 8, 2010, and No. 2011-148896, filed on Jul. 5, 2011 the entirety of which is hereby incorporated by reference.

What is claimed is:

1. A fluid ejection device comprising:
a pressure chamber;
an actuator having a displacement plane that varies the volume of the pressure chamber;
a delivery channel pipe communicating with the pressure chamber;
a first reflection surface of pressure wave formed as part of a paraboloid of revolution that reflects a plane pressure wave by displacement of the actuator, the plane pressure wave propagating through the pressure chamber; and
a second reflection surface of pressure wave formed as part of a paraboloid of revolution or an ellipsoid of revolution which is disposed so as to face the first reflection surface of pressure wave,
wherein
the first reflection surface of pressure wave and the second reflection surface of pressure wave have a common first focus, and
a pressure wave reflected from the second reflection surface of pressure wave propagates through the delivery channel pipe and ejects fluid.

2. The fluid ejection device according to claim 1, wherein a central axis of rotation of the first reflection surface of pressure wave and a central axis of rotation of the second reflection surface of pressure wave are nearly parallel to each other.

3. The fluid ejection device according to claim 2, wherein the central axis of rotation of the first reflection surface of pressure wave and the central axis of rotation of the second reflection surface of pressure wave coincide with each other.

4. The fluid ejection device according to claim 1, wherein a central axis of rotation of the first reflection surface of pressure wave and a central axis of rotation of the second reflection surface of pressure wave are not parallel to each other.

5. The fluid ejection device according to claim 1, wherein a central axis of the displacement plane of the actuator and a central axis of rotation of the first reflection surface of pressure wave are nearly parallel to each other, and a central axis of the delivery channel pipe and a central axis of rotation of the second reflection surface of pressure wave are nearly parallel to each other.

6. The fluid ejection device according to claim 5, wherein the central axis of the displacement plane of the actuator and the central axis of rotation of the first reflection surface of pressure wave coincide with each other, and the central axis of the delivery channel pipe and the central axis of rotation of the second reflection surface of pressure wave coincide with each other.

7. The fluid ejection device according to claim 5, wherein the central axis of the displacement plane of the actuator and the central axis of rotation of the first reflection surface of pressure wave are away from each other, and the central axis of the delivery channel pipe and the central axis of rotation of the second reflection surface of pressure wave are away from each other.

8. The fluid ejection device according to claim 1, wherein a second focus of the ellipsoid of revolution of the second reflection surface of pressure wave is disposed inside the delivery channel pipe.

9. A medical device including the fluid ejection device according to claim 1.

10. A medical device including the fluid ejection device according to claim 2.

11. A medical device including the fluid ejection device according to claim 3.

12. A medical device including the fluid ejection device according to claim 4.

13. A medical device including the fluid ejection device according to claim 5.

14. A medical device including the fluid ejection device according to claim 6.

15. A medical device including the fluid ejection device according to claim 7.

16. A medical device including the fluid ejection device according to claim 8.

* * * * *